United States Patent [19]

Grey et al.

[11] 4,346,240

[45] Aug. 24, 1982

[54] HYDROGENATION OF ESTERS USING ALKALI DOPED HETEROGENEOUS GROUP VIII TRANSITION METAL CATALYSTS

[75] Inventors: Roger A. Grey, Denville; Guido P. Pez, Boonton, both of N.J.

[73] Assignee: Allied Corporation, Morris Township, Morris County, N.J.

[21] Appl. No.: 307,031

[22] Filed: Sep. 29, 1981

Related U.S. Application Data

[63] Continuation of Ser. No. 132,917, Mar. 24, 1980, abandoned.

[51] Int. Cl.$^3$ .............................................. C07C 31/38
[52] U.S. Cl. .................................... 568/842; 568/799; 568/735; 568/814; 568/821; 568/822; 568/832; 568/834; 568/864; 568/885; 560/231; 560/234
[58] Field of Search ............... 568/799, 735, 814, 821, 568/822, 842, 832, 834, 864, 885; 560/234, 231

[56] References Cited

U.S. PATENT DOCUMENTS

| | | |
|---|---|---|
| 3,076,810 | 2/1963 | Duggan et al. . |
| 3,770,658 | 11/1973 | Ozaki et al. . |
| 4,072,726 | 2/1978 | Nychka et al. . |
| 4,142,993 | 3/1979 | Elofson et al. . |
| 4,154,751 | 5/1979 | McVicker et al. . |
| 4,164,515 | 8/1979 | Von Peppen et al. . |
| 4,232,170 | 11/1980 | Grey et al. . |

FOREIGN PATENT DOCUMENTS 356731 9/1931 United Kingdom .

*Primary Examiner*—Howard T. Mars
*Attorney, Agent, or Firm*—Alan M. Doernberg; Gerhard H. Fuchs

[57] ABSTRACT

A novel class of heterogeneous catalysts, containing Group VIII transition metals in combination with alkali organic compounds is prepared, such as potassium naphthalene on ruthenium on carbon. The catalysts are useful as heterogeneous catalysts in the hydrogenation of carboxylic acid esters. A process for producing the materials is described. The catalysts permit the process of the hydrogenation of carboxylic acid esters to primary alcohols to be conducted with the ester in the liquid phase at a temperature not exceeding about 150° C. with high selectivity. Catalysts of Group VIII transition metals and alkali metal on carbon are also useful in such processes.

32 Claims, No Drawings

HYDROGENATION OF ESTERS USING ALKALI DOPED HETEROGENEOUS GROUP VIII TRANSITION METAL CATALYSTS

This is a continuation of application Ser. No. 132,917, filed Mar. 24, 1980, now abandoned.

DESCRIPTION

BACKGROUND OF THE INVENTION

1. Field of the Invention

This invention relates to a process for hydrogenating carboxylic acid esters to primary alcohols in solution under mild conditions utilizing alkali doped Group VIII metal catalysts supported on carbon.

2. Brief Description of the Background of the Invention Including Prior Art

Carboxylic acid esters, as a class, are not readily susceptible to hydrogenation to produce primary alcohols under mild conditions. Generally, severe conditions are required, such as temperatures well above 150° C. together with reaction pressures in the order of 13.8 MPa to 20.7 MPa (2000–3000 psig). In addition, the hydrogenation process generally requires a catalyst which is frequently not selective, such as Raney nickel, copper-chromite, or zinc-chromium oxide. See *Organic Reactions*, Vol. 8, pages 1–27 (John Wiley, 1954).

Catalytic hydrogenation of carboxylic acid esters represents an important industrial source of primary alcohols, which are useful in a wide variety of known applications such as in producing gums, resins, perfumes, wetting agents and the like. For example, 1-decanol is commercially produced by catalytic hydrogenation of coconut oil fatty acids and their esters under high pressure. Sulfonated derivatives of 1-decanol are useful as surface active agents. Also, 2,2,2-trifluoroethanol, $CF_3CH_2OH$, useful as an intermediate in producing the anesthetic, $CF_3CHClOCHF_2$, is produced by the heterogeneous catalytic hydrogenation of 2,2,2-trifluoroethyl trifluoroacetate, $CF_3COOCH_2CF_3$, as described in U.S. Pat. No. 4,072,726 (Nychka et al. to Allied Chemical Corporation, 1978).

A. Ozaki et al. in U.S. Pat. No. 3,770,658 issued Nov. 6, 1973 disclose a catalyst comprising at least one element selected from the group consisting of transition metals belonging to VI-B group, VII-B group and VIII group of the Periodic Table and at least one element selected from the group consisting of alkali metals belonging to the I-A group of the Periodic Table, both elements being substantially in the metallic state.

This catalyst has not been employed in the hydrogenation of esters.

An example of soluble hydrogenation catalysts is disclosed in our copending, commonly assigned United States patent application Ser. No. 070,583 filed Aug. 29, 1979 which discloses a method for preparing anionic group VIII metal hydride complexes by reacting a neutral group VIII metal complex, or adduct thereof, with a group IA metal cation radical anion complex also called "metal arene" such as potassium naphthalene, in a solvent therefor, such as tetrahydrofuran or diethyl ether. New and improved catalysts for catalytic hydrogenation of carboxylic esters to primary alcohols are constantly being searched for.

SUMMARY OF THE INVENTION

The present invention concerns a method for preparing a catalyst comprising contacting a group VIII metal deposited on carbon with a member of the group consisting of alkali metal arenes, alkali metal ketyls, alkali metal alkoxides and their mixtures in the presence of a polar solvent.

The present invention also includes a solid catalyst composition consisting essentially of about 0.5 to about 15 weight percent of at least one Group VIII transition metal, about 1 to about 25 weight percent of at least one alkali metal cation, about 1.5 to about 75 weight percent of an anion selected from the group consisting of arene radical anions, ketyls, alkoxides and mixtures thereof, and the balance a support comprising high surface area carbon.

The present invention also includes two hydrogenation processes wherein a carboxylic acid monoester is reacted in the liquid phase with a gaseous hydrogen in the presence of a solid catalyst at a temperature not exceeding about 150° C. In the first process, the solid catalyst is the solid catalyst composition of the present invention. In the second process the solid catalyst is a composition consisting essentially of about 0.3 to about 99 weight percent of at least one Group VIII transition metal, about 0.1 to about 50 weight percent of at least one alkali metal and the balance an inert support comprising high surface area carbon.

The present process can hydrogenate an ester group in a cyclic or acyclic saturated aliphatic monoester, thereby converting the acid moiety of said ester to a primary alcohol group. The present process is particularly applicable to hydrogenating esters with an aromatic acid moiety such as methyl benzoate in that the acyl carbon can be hydrogenated to an alcohol without hydrogenating the aromatic ring, i.e. to benzyl alcohol rather than to cyclohexyl methanol.

DETAILED DESCRIPTION OF THE INVENTION

In defining the catalyst composition of the present invention and the catalyst for the present processes, weight proportions of metals are given and, in some instances, weight proportions of an anion are given. High surface area carbon, e.g. activated carbon, is indicated as a support. The amount of such carbon required or permitted is that sufficient to give a high surface area to the other materials. It should not, however, be considered that the carbon is unessential since, in fact, the advantages of the present invention are not achieved when such carbon is not present. It is permissible, however, to employ inert materials, or even other activator or promoter materials, as well as carbon as additional support components.

The present invention is not limited to catalysts and processes wherein the Group VIII and alkali metals are in a neutral or metallic valence state. Rather it is believed that the alkali metal and the Group VIII metal are in various valence states within the range +1 to −1 in the active catalyst. Hydrogenation reaction conditions are capable of converting these metals to such valence states from some, but not all other valence states.

The alkali metal is introduced into the catalyst either as a metal or as a cation with a very strong base, e.g. in combination with the anions recited as part of the novel catalyst composition. The term "consisting essentially of" is intended to exclude from the composition materials which are acidic in character and can neutralize the strongly basic nature of the above anions. In the catalyst for the second process, which has no such anion, it is believed that a similar function may be performed either by the alkoxide formed once alcohols begin to appear as the result of hydrogenation, or by arene radical anions within the carbon support.

The term "liquid phase" is used to describe the hydrogenation processes to indicate that the ester is either dissolved in a solvent or used as a neat liquid. The catalyst is in the solid phase and the hydrogen is partitioned between the gas phase, the liquid phase and the solid phase.

Group VIII metal deposited on carbon

A number of ways well known in the art can be employed to deposit the group VIII metal onto the carbon. Soluble salts of group VIII transition metals can be dissolved in an aqueous solution. Then carbon is added to the solution and the solution is stirred for a time period of about 10 minutes to 48 hours. Then the water is removed, e.g. by vacuum evaporation.

For example a group VIII metal halide can be distributed on carbon by an aqueous solution with the water being removed by heating and evacuation. The deposited metal halide is then reduced to the metal at about 300° C. to 500° C. in a reducing atmosphere. A preferred reducing atmosphere is provided by molecular hydrogen and a preferred temperature range is from about 350° C. to 450° C.

The group VIII metal on carbon can then be activated for catalyzing hydrogenation reactions of esters by reaction with group I metals or certain group I metal compounds.

Alkali metal activated group VIII transition metal carbon catalysts

Various ways are available for activating the group VIII metal on carbon with group I metals. For obtaining group VIII transition metal catalysts activated by an alkali metal, the group VIII metal dispersed on carbon is reacted with the desired alkali metal in an inert or reducing atmosphere or in vacuum. Preferably the alkali metal is dispersed on the group VIII metal carbon by condensation from the vapor phase. This can be achieved by heating the alkali metal in the presence of the group VIII metal on carbon to temperatures from about 200° C. to 500° C. and preferably from 350° C. to 450° C., under vacuum or in an inert atmosphere.

Alternatively alkali metal activated group VIII metal-carbon catalysts can be obtained by employing liquid ammonia as a solvent medium for the alkali metal, which is then contacted with the group VIII metal-carbon composition. The solution is filtered after sufficient reaction time and then the ammonia is evaporated by slowly heating under reduced pressure (vacuum) to temperatures of about 120° C. to 160° C. until the ammonia evaporation terminates.

Alkali metal compound activated group VIII transition metal carbon catalysts Catalysts made according to the present invention include group VIII transition metal carbon catalysts activated with alkali metal arenes, alkali metal ketyls, alkali metal alkoxides and their mixtures.

For obtaining group VIII transition metal catalysts activated by an alkali metal arene, the group VIII transition metal on carbon catalyst should preferably be pretreated with hydrogen at 350°-450° C. A metal arene is prepared by reacting an alkali metal (e.g. sodium) with an arene (e.g. naphthalene) in an inert polar solvent. The pretreated catalyst is then contacted with the alkali metal arene in the presence of an inert polar solvent. The reaction is performed at a temperature of from about $-100°$ C. to 100° C. Thereafter, the resultant catalyst can be washed with the polar solvent to remove any free arene or free alkali metal arene. The solvent may be removed and the preparation then dried in vacuum; or, alternatively, the catalyst can be used in the solvent in which it is prepared (i.e. in situ).

For obtaining group VIII transition metal catalysts activated by an alkali metal ketyl, the following procedure may be used. The alkali metal ketyl can be prepared by reacting the alkali metal with the ketone in a polar inert solvent at a suitable temperature for a sufficient time. In general, the reaction temperature can be from about $-100°$ C. to 100° C.

The alkali metal ketyl activated group VIII transition metal catalysts are preferably prepared by dispersing the group VIII transition metal-carbon composition in an inert polar solvent and then adding the alkali metal ketyl, optionally also dissolved in an inert polar solvent. The reaction mixture is preferably agitated and kept at a temperature of about $-100°$ C. to 100° C. for sufficient time to complete the reaction, such as 1-70 hours. The solid catalyst formed can be washed with an inert polar solvent to remove excess ketyl or used in situ.

For obtaining group VIII transition metal catalysts activated by an alkali metal alkoxide, the group VIII transition metal on carbon catalyst can be contacted with an alkali metal alkoxide in the presence of an inert polar solvent. The reaction is performed at a temperature from about $-100°$ C. to 100° C. These catalysts are preferably used in situ (without removing solvent).

Polar inert solvents useful in the preparation of the catalysts include tetrahydrofuran, tetrahydropyran, dimethyl ether, diethyl ether, dioxane, 1,2-dimethoxy ethane and other polyethers which lack free hydroxyls. The term "solvent" is intended to mean a liquid which dissolves the alkali metal-containing reactant, since the Group VIII metal on carbon remains in the solid phase. Tetrahydrofuran and 1,2-dimethoxyethane are preferred.

The Group VIII metal present in the subject compositions include iron, cobalt, nickel, ruthenium, rhodium, palladium, iridium and platinum and preferably ruthenium, rhodium, palladium and platinum, especially ruthenium and rhodium. The alkali metal may be lithium, sodium, potassium, rubidium or cesium, preferably lithium, sodium or potassium, most preferably potassium.

Representative examples of alkoxides applicable in the invention compositions are triphenylmethoxy, diphenylmethylmethoxy, 2,2-diphenylethoxy, 1,2,2-triphenyl ethoxy, diphenylmethylmethoxy, trimethylnaphthyl, triethylnaphthyl, trioctadecylmethoxy, tri-n-octylmethoxy, triisopropylmethoxy, tri-secondary-butylmethoxy, tricyclohexylmethoxy, tri(pentamethylphenyl)methoxy, tri(p-tolyl)methoxy, tri(p-n-octadecylphenyl)methoxy, tri(p-n-octylphenyl)methoxy, tri(2-phenethyl)methoxy, tri-benzylmethoxy tri(2-phenylisooctadecyl)methoxy, tri-(p-methoxyphenyl)methoxy, tri(2-methoxyethyl)methoxy, tri(p-tertiary-butoxyphenyl)methoxy, 1,2,3-triphenylpropoxy, dimethylanthryl 1,2-diphenyldioxy(1,2), phenoxy, benzoxy, naphthoxy, anthroxy and phenanthroxy. Acyclic alkoxy is preferred. Most preferred are methoxy, ethoxy and trifluoroethoxy, with other $C_1$ and $C_2$ straight chain alkoxy or fluorinated alkoxy being also preferred.

The arene radical anion is the radical anion of an aromatic compound containing 6 to 24 carbon atoms and can be formed from benzene, toluene, naphthalene, biphenyl, xylene, anthracene, phenanthrene, their aryl substituted derivatives, and the like. Substituents on any aryl ring which tend to donate electrons to the ring or form relative groups under conditions of catalyst preparation or hydrogenation are not suitable. In general only inert aliphatic, ether or dialkylamino substituents are permitted, and unsubstituted arenes are preferred. The most preferred aromatic is naphthalene. Arene radical anions from biphenyl, anthracene and phenanthrene are also somewhat preferred. Representative examples of alkali metal radical anion compounds include lithium naphthalene, sodium naphthalene, potassium naphthalene, cesium naphthalene and potassium biphenyl. Such alkali metal arene radical anion compounds can be prepared by reacting an alkali metal with a suitable aromatic compound (i.e. arene) in a suitable inert polar solvent. Thus a preferred alkali metal arene radical anion compound is an alkali metal (e.g. potassium) naphthalene prepared by reacting the metal with naphthalene in an inert polar solvent such as tetrahydrofuran. Aryl type substituents of the arenes include biphenyl, benzyl, tolyl, xylyl, cumyl, naphthyl, anthryl, phenanthryl and diphenyl.

The alkali metal ketyl activators include alkali metal ketyl wherein the ketyl part derives from a keto group attached to at least one aromatic group and preferably attached to two aromatic groups. Examples for such ketones include benzophenone, phenyl tert-butyl ketone, phenyl naphthyl ketone, dinaphthyl ketone. A preferred ketyl is the ketyl prepared from benzophenone and an alkali metal.

If a ketone has a carbon adjacent the carbonyl with a hydrogen bonded to the adjacent carbon, then the reaction product will be an alkali metal enolate rather than an alkali metal ketyl. For purposes of the present invention, such alkali metal enolates are equivalent to alkali metal ketyls. Thus alkali metal enolates prepared by reacting an alkali metal such as potassium with a ketone such as acetone, methyl phenyl ketone, cyclohexyl phenyl ketone, phenyl isopropyl ketone and the like are suitable and may, because of the tautomerism between structures, be considered equivalent to ketyls.

Furthermore, alkali metals dissolved in liquid ammonia can also be used to prepare part of the catalysts of the present invention.

To prepare catalysts useful for the second process of the invention, the group VIII transition metal should be supported on a high surface area carbon and then reacted with an alkali metal dopant. The Group VIII transition metal part is placed in a state substantially free from materials leading to decomposition of the strongly nucleophilic doping reagent.

After contacting the supported Group VIII transition metal with the alkali metal dopant, the resulting mixture is reacted at a temperature of from about $-100°$ C. to $100°$ C., with temperatures from about $-78°$ C. to $25°$ C. preferred, in a polar solvent, usually an ether.

In the novel catalysts and first process of the present invention, the broad weight percent ranges set forth above—about 0.1 to about 15 percent Group VIII transition metal, about 1 to about 50 weight percent alkali metal cation and about 2 to about 50 weight percent anion—are intended to accommodate the varying densities and sizes of the various possibilities. For lithium, for example, about 1 to about 5% by weight is preferred, and about 2 to about 3% is more preferred. For sodium and potassium, about 2 to about 20% is preferred, with about 7 to about 10% being more preferred for sodium and about 8 to about 12% being more preferred for potassium. For cesium, about 10 to about 50% is preferred, and about 40 to about 50% is more preferred. All of the above percentages are by weight. The balance is a support which can be essentially all activated carbon.

Anions are likely to be present in molar proportions no more than the alkali metal. A lesser amount of arene can be introduced by reacting the supported Group VIII transition metal with both free alkali metal and alkali metal compound with any of the anions discussed above.

In the second process of the invention, the preferred broad percentages are about 0.1 to about 25% Group VIII transition metal, about 0.5 to about 60% alkali metal and the balance support. Preferred ranges are about 1 to about 5% for lithium, about 2 to about 25% for sodium or potassium and about 10 to about 50% for cesium. More preferred are about 2 to about 3% for lithium, about 7 to about 10% for sodium, about 8 to about 12% for potassium and about 40 to about 50% for cesium. Again, the balance is a support which can be essentially activated carbon. In both cases, if granular catalyst particles are used, then the above proportions need only refer to the exterior layer of the surface which is in intimate contact with the reactants.

Apparatus for Catalyst Formation

Apparatus which is used to carry out the process of catalyst formation can be of any conventional type in which the steps of addition of reagents, heating, cooling, isolation and purification procedures can be carried out under an inert dry atmosphere and include the use of conventional dry-boxes, glove-bags and conventional vacuum equipment. Apparatus which is useful is an H-shaped hollow glass evacuable cell in which the horizontal portion serves as a filtering device and the vertical sides of the "H" serve as the reaction vessel.

Catalytic Hydrogenation of Esters

By the terms "hydrogenation catalyst" and "catalyst composition" as used herein, is meant the compositions described above.

One aspect of novelty of these improved processes is the discovery that the subject compositions are surprisingly effective catalysts for the respective catalytic heterogeneous hydrogenations in which the esters are in the liquid phase (neat or otherwise). A preferred solvent for the esters is tetrahydrofuran.

Carboxylic acid esters, comprised of an acid moiety and alcohol moiety (and by the term "alcohol moiety", is meant to include aromatic hydroxy moiety, e.g., phenols and naphthols as well) which are applicable in this invention process, include those wherein the acid moiety is derived from a $C_2$-$C_{18}$ linear or branched alkyl monocarboxylic acid, $C_2$-$C_6$ linear or branched alkyl dicarboxylic acid, $C_7$-$C_8$ cycloalkyl monocarboxylic acid, $C_2$-$C_4$ fluorinated monocarboxylic acid, containing 1-7 fluorine atoms, and said alcohol moiety of said ester is derived from a $C_1$-$C_4$ linear or branched alkyl alcohol, $C_1$-$C_4$ linear or branched fluorinated alcohol, containing 1-7 fluorine atoms, $C_7$-$C_9$ aralkyl alcohol, or $C_6$-$C_{10}$ aromatic hydroxy compound.

Representative examples of monocarboxylic acids providing the acid moiety in said ester are acetic acid, propionic acid, butyric acid, isobutyric acid, n-hexanoic acid, n-heptanoic acid, n-octanoic acid, n-nonanoic acid, n-decanoic acid, n-pentadecanoic acid, n-octadecanoic acid, benzoic acid, cyclohexylacetic acid, fluoroacetic acid, difluoroacetic acid, trifluoroacetic acid, trifluoropropionic acid and trifluorobutyric acid, and the like. Preferred acids are monocarboxylic aliphatic acids and their fluorinated derivatives.

Representative examples of alcohols and aromatic hydroxy compounds providing the alcohol moiety in said ester are methanol, ethanol, propanol, isopropanol, n-butanol, isobutanol, sec-butanol, t-butanol, 2,2,2-trifluoroethanol (hereinafter referred to as "tri-fluoroethanol"), monofluoromethanol, difluoromethanol, 1,3-difluoro-2-propanol, benzyl alcohol, phenethyl alcohol, phenol, 2-naphthol, and the like.

It is to be understood that esters produced from combinations of the above-described acids and alcohols in the known manner are deemed to be applicable within the scope of this invention process. Representative examples of esters useful in the invention process are methyl acetate, ethyl acetate, methyl n-octadecanoate, isobutyl decanoate, t-butylnonoate, phenyl acetate, 2-naphthyl propionate, methyl cyclohexylcarboxylate, ethyl cyclohexylacetate, n-butyl fluoroacetate, methyl difluoroacetate, n-propyl trifluoropropionate, methyl trifluorobutyrate, isopropyl acetate, sec-butyl propionate, fluoromethyl acetate, difluoromethyl acetate, 1,3-difluoro-2-propyl octanoate, benzyl acetate, phenethyl acetate, methyl trifluoroacetate and trifluoroethyl trifluoroacetate. Preferred examples of esters in the invention process are methyl acetate, ethyl acetate, methyl propionate, methyl trifluoroacetate and trifluoroethyl trifluoroacetate and methyl benzoate. Particularly preferred ester in the invention process is trifluoroethyl trifluoroacetate.

In addition to the esters described hereinabove, cyclic "inner esters", i.e. lactones, are also applicable in the invention process, which can be hydrogenated to yield diols, useful in the synthesis of polyesters. The scope of lactones applicable in the invention process include $C_3$–$C_{12}$ alkyl lactones, such as propiolactone, butyrolactone, valerolactone, octanoic lactone, caprolactone and 1,12-dodecalactone. Preferred are alkyl lactones in which the lactone functional group is formed between the first and terminal carbon atoms in the precursor hydroxy alkyl carboxylic acid. Thus, caprolactone can be hydrogenated to yield 1,6-hexanediol and the above-described lactones will yield diols in like manner.

The amount of carboxylic acid ester substrate present in the process is not critical and is generally about 1 to 100,000 parts by weight of substrate per part of catalyst composition and preferably, about 10 to 1,000 parts by weight of ester substrate per part of catalyst composition. However, larger or smaller amounts of substrate may effectively be used.

The process can be conducted in the neat state, i.e. no solvent, providing said ester is liquid at the reaction temperature employed. However, it is preferred to conduct the reaction in the presence of an inert solvent for the carboxylic ester substrate.

Solvents which are applicable in the invention process must be inert toward hydrogenation under the reaction conditions and should preferably be anhydrous, and include $C_6$–$C_{12}$ benzenoid hydrocarbons, and $C_2$–$C_{18}$ alkyl derivatives thereof, $C_5$–$C_{10}$ linear or branched saturated aliphatic or alicyclic hydrocarbons, $C_4$–$C_6$ saturated aliphatic cyclic mono- or diethers and $C_2$–$C_6$ linear or branched saturated aliphatic mono- or diethers, $C_7$–$C_{14}$ aromatic ethers, or mixtures thereof.

Representative examples of specific solvents useful in the invention process of ester hydrogenation are benzene, toluene, xylene, hexamethylbenzene, biphenyl, n-octadecylbenzene, pentene, cyclopentane, cyclohexane, methylcyclohexane, hexane, isooctane, decane, cyclodecane, tetrahydrofuran, p-dioxane, 2,5-dimethyltetrahydrofuran, methyl tetrahydrofurfuryl ether, dimethyl ether, 1,2-dimethoxyethane, diglyme, diethylether, diisopropyl ether, anisole, diphenyl ether, and mixtures thereof.

Preferred solvents in the process of the invention are toluene, benzene, cyclohexane, hexane, tetrahydrofuran, p-dioxane, diethyl ether or 1,2-dimethoxyethane. A particularly preferred solvent is tetrahydrofuran.

The amount of solvent, when used, is not critical provided sufficient solvent is present to dissolve the carboxylic acid ester substrate and to initiate and maintain the hydrogenation reaction. In general, about 1 to 100 parts by weight of solvent per part of ester is used, although not limited thereto, larger or smaller amounts being effective with the above proviso.

Temperature in the process is normally in the range from about 0° C., to about 150° C. and preferably in the range of about 25° to 100° C. However, higher temperatures can also be employed and are considered to be equivalent to the stated preferred ranges.

The pressure in the reaction process may be 100 to 1100 kPa (0 psig to 150 psig) at the reaction temperature; however, higher pressures can be employed and may improve the conversion of esters to alcohols as illustrated to Example 23 below.

The process is conducted under an atmosphere containing hydrogen gas, being the active reducing agent. The atmosphere above the reaction mixture can also contain an inert gas such as nitrogen, argon, mixtures thereof, and the like, as long as sufficient hydrogen gas is present to maintain the hydrogenation reaction. The process can be conducted in conventional batch reactors (e.g. a stirred tank) or flow reactors (e.g. a trickle-bed reactor).

Conversions of esters in the process range from 5 to 100% of theory based on the starting amount of ester substrate and the particular ester used.

Selectivities in the process for production of primary alcohols from esters are in the range of about 90 to 100%, being defined as (moles primary alcohol produced/divided by moles ester hydrogenated)×100.

The product primary alcohol can be isolated from the process and purified by conventional methods such as extraction, followed by fractional distillation or column or gas chromatographic techniques.

Apparatus for conducting ester hydrogenation process can be any conventional pressure apparatus, glass or steel, in which the operations of charging the reactant materials, heating, cooling, stirring, introduction of hydrogen gas, isolation and purification the final products can be conducted substantially in the absence of air and moisture. Such apparatus and procedure for carrying out the invention process will be obvious to one skilled in the art from this disclosure.

The catalysts of the present invention are effective at milder conditions (e.g. 25° C.) than is known for other heterogeneous catalysts such as copper chromium oxides.

This process is useful in reducing esters, which are produced in the "oxo" reaction, to the corresponding alcohols.

This process is useful to reduce methyl acetate (formed from methanol and carbon monoxide).

This process is useful for the production of 2,2,2-trifluoroethanol from trifluoroethyl trifluoroacetate and hydrogen.

The following examples are illustrative of the best mode of carrying out the invention as contemplated by us and should not be construed as being limitations on the scope and spirit of the instant invention.

EXAMPLE 1

Preparation of 5% Ruthenium on Carbon 0.4 g of ruthenium trichloride hydrate obtained from Matthey Bishop Company was dissolved in 20 mL of distilled water. To this 3 g of DARCO Activated Carbon Grade G-60 special from ICI Americas, Specialty Chemical Division, Wilmington, Del., ("DARCO" being their registered trademark), was added and stirred in at room temperature for 20 hours. The water was removed in vacuum using a rotary evaporator and the solids heated in a flow reactor under hydrogen at 200° C. for 2 hours, 300° C. for 20 hours and 425° C. for $\frac{1}{2}$ hour. The solids were then stored in an argon dry box.

EXAMPLE 2

Preparation of Potassium/Ruthenium on Carbon

Potassium/ruthenium on carbon was prepared as follows. A 90 mL Fisher and Porter pressure tube was loaded (under argon) with 200 mg of potassium metal. The tube was attached to a dynamic vacuum and heated in such a way that the potassium was dispersed over the inside surface of the lower 2.5 cm of the tube. Commercial 5% Ru on carbon (obtained from Strem or from Engelhard) was dried by heating first at 250° C. (2 hours) and then for 16 hours at 400° C. in a current of hydrogen. This Ru/C (1.0 g) was added to the pressure tube, covering most of the sublimed K metal. The mixture was then heated in an electric oven (under a dynamic vacuum) at 400° C. for $\frac{1}{2}$ hour, cooled to R.T., shaken well and the heating repeated. The catalyst is very air sensitive and was handled under an atmosphere of pure argon. Hydrolysis of 100 mg of this K/Ru/C gave KOH; by subsequent titration with HCl, the catalyst was found to contain 100.9 mg K/g of catalyst.

EXAMPLE 3

Preparation of $Ru/C/K^+C_{10}H_8^-$ And Similar $Li^+$, $Na^+$ and $Cs^+$-doped Catalysts A metal halide such as $RuCl_3.xH_2O$ or $RhCl_3.3H_2O$ was dispersed on carbon in aqueous solution. The water was removed in vacuo by heating. The rhodium or ruthenium chloride was then reduced to the corresponding metal by heating up to 400° C. under a hydrogen purge. Potassium naphthalene was prepared by stirring together equimolar amounts of naphthalene and potassium metal in tetrahydrofuran (THF) for 16 hours at room temperature followed by evaporation of the THF in vacuo. Lithium and cesium naphthalenes were prepared in a corresponding manner by substituting the appropriate metal for potassium metal. Sodium naphthalene was prepared without evaporation, but was used as a solution. This supported rhodium or ruthenium catalyst was then treated with the potassium naphthalene in THF solution.

Alternatively, the dried, supported metal halide, nitrate, etc., can be treated with three equivalents more than the usual amount potassium naphthalene and thus reduced to the metallic form in situ with potassium naphthalene instead of hydrogen and heat.

An H-shaped tube with horizontal portion containing a filter frit was charged with 1 g of 5% Ru/C (from Engelhard, previously dried under $H_2$ for 16 hours at 200° C., 7 hours at 325° C. and $\frac{1}{2}$ hour at 410° C.) and 1 g of solid potassium naphthalene (20 weight percent potassium), each loaded under argon into one leg of the H-tube. Tetrahydrofuran (25 mL) was added to the H-tube and allowed to stir at room temperature for one hour. The reaction mixture was filtered, the $Ru/C/K^+C_{10}H_8^-$ washed with two 10 mL portions of tetrahydrofuran and dried in vacuo. An elemental analysis gave 11.85% w/w potassium. Corresponding lithium, sodium and cesium doped catalysts were prepared in a similar manner using the appropriate alkali metal naphthalene, using the sodium naphthalene solution as such.

EXAMPLE 4

Preparation of Rh/C Using Potassium Benzphenone

One side of an H-shaped tube containing a filter disk was charged with 0.5 g of $K^+Ph_2CO^-$ (prepared by the reaction of equal molar amounts of potassium and benzophenone at 25° C. for 16 hours in THF solution followed by removal of the THF in vacuo), 0.5 g of 5% Rh/C and 30 mL of THF. The reaction mixture was stirred at 25° C. for 16 hours and filtered. The solids were then washed exhaustively with THF and dried in vacuo giving 0.6 g of $Rh/C/K^+Ph_2CO^-$.

EXAMPLE 5

Preparation of Lithium Doped Rhodium on Carbon Using Liquid $NH_3$

A sample of 5% Rh/C was treated with $H_2$ gas in a similar manner as described in Example #1. The solid (0.93 g) was loaded in one leg of a H-shaped apparatus; the other leg was charged with 50 mg of lithium powder. All manipulations were done in an argon atmosphere. The apparatus was then transferred to a vacuum line and pure, dry ammonia (5 mL) was condensed into the lithium containing portion of the apparatus. The $Li/NH_3$ slurry was stirred at −65° C. until all the metal had dissolved to yield a deep blue solution. The solution was then poured immediately onto the Rh/C, where it was almost immediately decolorized by absorption and reaction with the solid. After stirring at −65° C. for 10 minutes, the solution was filtered and the residue washed with 2×5 mL portions of liquid $NH_3$. Ammonia in the filtrate was pumped off and the dark residue was dried by heating slowly in a dynamic vacuum first at 90° C. ($3\frac{1}{2}$ hours) then at 160° C. ($3\frac{1}{2}$ hours) until no traces of $NH_3$ evolution were noted.

Analyses:
 Li (catalyst)=3.98% w/w
 Li (Rh/C)=0.0% w/w

EXAMPLE 6

Preparation of Sodium Doped Rhodium on Carbon Using Liquid NH₃

The same technique was used as described in Example #1 except that sodium metal 95 mg and 1.0 g of Rh/C were used.

The final Na/Rh/C product was analyzed for total sodium and 8.0% w/w Na was found. The product was then analyzed for sodium metal by reaction with H₂O. The hydrogen gas evolved was measured and found to correspond to an equivalent of 1.6% w/w sodium metal. No sodium was detected by elemental analysis of the original Rh/C.

EXAMPLE 7

Catalytic Hydrogenation of Trifluoroethyl Trifluoroacetate using Ru/C/CF₃CH₂O⁻K⁺

A pressure tube was charged with 50 mg of 5% Ru/C and 20 mg of CF₃CH₂O⁻K⁺ and tetrahydrofuran (3 mL). The mixture was stirred at room temperature for 20 minutes and 0.6 mL (0.838) of trifluoroethyl trifluoroacetate was added. The reaction mixture was pressurized to 720 kPa (90 psig) of hydrogen and allowed to react at 56° C. for 2 hours. Analysis of the reaction mixture by gas chromatography showed complete conversion of the ester to trifluoroethanol in high selectivity (>96%).

EXAMPLE 8

Catalytic Hydrogenation of Trifluoroethyl Trifluoroacetate Using Ru/C/K

A pressure tube was charged with 40 mg of Ru/C/K, prepared as in Example 2, (5 weight percent ruthenium, 4 weight percent potassium), tetrahydrofuran (3 mL) and 1.2 mL (1.67 g) of trifluoroethyl trifluoroacetate. The reaction mixture was pressurized to 1150 kPa (150 psig) of hydrogen allowed to react at 56° C. for 24 hours. Analysis of the reaction mixture showed complete conversion of the ester to trifluoroethanol in high selectivity (>96%).

EXAMPLE 9

Catalytic Hydrogenation of Methyl Acetate Using Ru/C/K

The pressure tube was charged with 50 mg of Ru/C/K prepared as in Example 2 (5 weight percent ruthenium, 10 weight percent potassium), tetrahydrofuran (3 mL) and 0.3 mL (0.28 g) of methyl acetate. The reaction mixture was pressurized to 720 kPa (90 psig) of hydrogen and allowed to react at 60° C. for 24 hours. Analysis of the reaction mixture showed 32% conversion of the methyl acetate to methanol, ethanol and ethyl acetate.

EXAMPLE 10

Catalytic Hydrogenation of Methyl Acetate Using Ru/C/CH₃O⁻K⁺

A glass pressure tube was charged with 50 mg of Ru/C and 20 mg of CH₃O⁻K⁺, THF (3 mL) and 0.3 mL (0.28 g) of methyl acetate. The reaction mixture was pressurized to 720 kPa (90 psig) of hydrogen and allowed to react at 60° C. for 24 hours. Analysis of the reaction mixture showed 14% conversion of the methyl acetate to methanol, ethanol and ethyl acetate.

EXAMPLE 11

Catalytic Hydrogenation of Methyl Acetate Using Ru/C/K+C₁₀H₈⁻

A glass pressure tube was charged with 50 mg of hydrogen pretreated Ru/C (5 weight percent ruthenium) 50 mg of potassium naphthalene, tetrahydrofuran (3 mL) and 3 mL (0.28 g) of methyl acetate. The reaction mixture was pressurized to 720 kPa (90 psig) of hydrogen and allowed to react at 25° C. for 24 hours. Analysis of the reaction mixture showed 37% conversion of methyl acetate to methanol, ethanol and ethyl acetate.

EXAMPLE 12

Catalytic Hydrogenation of Methyl Acetate Using Rh/C/K+C₁₀H₈⁻

A glass pressure tube was charged with 100 mg of Rh/C/K+C₁₀H₈⁻ (11% weight percent potassium), prepared as in Example 3, tetrahydrofuran (3 mL) and 0.3 mL (0.28 g) methyl acetate. The reaction mixture was pressurized to 720 kPa (90 psig) of hydrogen and allowed to react at 75° C. for 16 hours. Analysis of the reaction mixture showed 53% conversion of methyl acetate to methanol, ethanol and ethyl acetate. By contrast, 100 mg of Rh/C alone under the same conditions or separately 100 mg of potassium naphthalene alone gave no hydrogenation products. Potassium naphthalene supported on carbon alone also did not catalyze the ester hydrogenation reaction.

EXAMPLE 13

Catalytic Hydrogenation of Methyl Benzoate Using Rh/C/K+C₁₀H₈⁻

A glass pressure tube was charged with 100 mg of Rh/C/K+C₁₀H₈⁻, prepared as in Example 3, tetrahydrofuran (3 mL) and 0.5 mL (0.55 g) of methyl benzoate. The reaction mixture was pressurized to 720 kPa (90 psig) of hydrogen and allowed to react at 25° C. for 24 hours. Analysis of the reaction mixture showed a 10% conversion of the methyl benzoate to methanol, benzyl alcohol and benzyl benzoate. This contrasts with a run using Rh/C alone as the catalyst in which at 64° C. in 24 hours, there was 90% conversion to carbomethoxycyclohexane with no benzyl alcohol observed.

EXAMPLE 14

Catalytic Hydrogenation of Methyl Acetate Using Rh/C/K+Ph₂CO⁻

A glass pressure tube was charged with 100 mg of Rh/C/K+Ph₂CO⁻, prepared as in Example 4 (2 weight percent rhodium, 5.6 weight percent potassium), tetrahydrofuran (3 mL) and methyl acetate 0.3 mL (0.28 g). The reaction mixture was pressurized to 720 kPa (90 psig) of hydrogen and allowed to react at 25° C. for 16 hours. Analysis of the reaction mixture by gas chromatography showed 49% conversion to ethanol, ethyl acetate and methanol.

EXAMPLE 15

Catalytic Hydrogenation of Methyl Acetate Using Rh/C/K Prepared from Potassium Dissolved in Liquid Ammonia A glass pressure tube was charged with 100 mg of Rh/C/K, prepared as in Example 5 (3 weight percent rhodium, 17 weight percent potassium), tetrahydrofuran (3 mL) and methylacetate 0.3 mL (0.28 g). The reaction mixture was pressurized to 720 kPa (90 psig) of hydrogen and allowed to react at 25° C. for 72 hours. Analysis of the reaction mixture by gas chromatography showed 42% conversion to ethanol, ethyl acetate and methanol.

EXAMPLE 16

Catalytic Hydrogenation of Methyl Acetate Using Rh/C/Na+$C_{10}H_8^-$

A glass pressure tube was charged with 100 mg of Rh/C/Na+$C_{10}H_8^-$ prepared as in Example 3 (6.7 weight percent sodium) and 0.3 mL (0.28 g) of methyl acetate. The reaction mixture was pressurized to 720 kPa (90 psig) of hydrogen and allowed to react at 25° C. for 20 hours. Analysis of the reaction mixture showed 20% conversion of the methyl acetate to ethanol, ethyl acetate and methanol.

EXAMPLE 17

Catalytic Hydrogenation of Methyl Acetate using a Mixture of Rh/C and C/K+$C_{10}H_8^-$ A glass pressure tube was charged with 50 mg of hydrogen pretreated Rh/C (5 weight percent rhodium); 200 mg C/K+$C_{10}H_8^-$ (2 weight percent potassium), 3 mL of tetrahydrofuran and 0.3 mL (0.28 g) of methyl acetate. The reaction was pressurized to 720 kPa (90 psig) of hydrogen and allowed to react at 25° C. for 20 hours to give 33% conversion of the methyl acetate to ethanol, ethyl acetate and methanol.

EXAMPLE 18

Catalytic Hydrogenation of Methyl Acetate Using Pd/C/K+$C_{10}H_8^-$

A glass pressure tube was charged with 100 mg of Pd/C/K+$C_{10}H_8^-$ prepared as in Example 3 (11.2 weight percent potassium), 3 mL of tetrahydrofuran and 0.3 mL (0.28 g) of methyl acetate. The reaction mixture was pressurized to 720 kPa (90 psig) of hydrogen and reacted at 25° C. for 20 hours to give 11% conversion of the methyl acetate to ethanol, ethyl acetate and methanol.

EXAMPLE 19

Catalytic Hydrogenation of Methyl Acetate Using Pt/C/K+$C_{10}H_8^-$

A glass pressure tube was charged with 100 mg of Pt/C/K+$C_{10}H_8^-$, prepared as in Example 3 (11.3 weight percent potassium), 3 mL of tetrahydrofuran and 0.3 mL (0.28 g) of methyl acetate. The reaction mixture was pressurized to 720 kPa (90 psig) of hydrogen and reacted at 25° C. for 20 hours to give 20% conversion of the methyl acetate to ethanol, ethyl acetate and methanol.

EXAMPLE 20

Catalytic Hydrogenation of Methyl Acetate Using Rh/C/Li

A glass pressure tube was charged with 100 mg of Rh/C/Li, prepared as in Example 5 (3.98 weight percent lithium) 3 mL of tetrahydrofuran and 0.3 mL (0.28 g) of methyl acetate. The reaction mixture was pressurized to 720 kPa (90 psig) of hydrogen and allowed to react at 25° C. for 20 hours to give 16% conversion of the methyl acetate to ethanol, ethyl acetate and methanol.

EXAMPLE 21

Catalytic Hydrogenation of Methyl Acetate Using Rh/C/Na

A glass pressure tube was charged with 100 mg of Rh/C/Na, prepared as in Example 6 (7.96 weight percent sodium) 3 mL of tetrahydrofuran and 0.3 mL (0.28 g) of methyl acetate. The reaction mixture was pressurized to 720 kPa (90 psig) of hydrogen and allowed to react at 25° C. for 20 hours to give 49% conversion of the methyl acetate to ethanol, ethyl acetate and methanol.

EXAMPLE 22

Catalytic Hydrogenation of Methyl Acetate Using Rh/C/Cs+$C_{10}H_8^-$

A glass pressure tube was charged with 100 mg of Rh/C/Cs+$C_{10}H_8^-$, prepared as in Example 3 (47 weight percent cesium) 3 mL of tetrahydrofuran and 0.3 mL (0.28 g) of methyl acetate. The reaction mixture was pressurized to 720 kPa (90 psig) of hydrogen and allowed to react at 88° C. for 20 hours to give a 24% conversion of methyl acetate to ethanol, ethyl acetate and methanol.

EXAMPLE 23

Catalytic Hydrogenation of Methyl Acetate Using Rh/C/K+$C_{10}H_8^-$

A stainless steel bobm was charged with 100 mg of Rh/C/K+$C_{10}H_8^-$, prepared as in Example 3 (11 weight percent potassium), 3 mL of tetrahydrofuran and 0.3 mL (0.28 g) of methyl acetate. The reaction mixture was pressurized to 990 psig (6830 kPa gauge) of hydrogen and allowed to react at 25° C. for 20 hours to give an 80% conversion of methyl acetate to ethanol, ethyl acetate and methanol.

EXAMPLE 24

Catalytic Hydrogen of Caprolactone Using Rh/C/K+$C_{10}H_8^-$

A glass pressure tube was charged with 100 mg of Rh/C/K+$CH_{10}H_8^-$, prepared as in Example 3, (11 weight percent potassium), 3 mL of tetrahydrofuran and 0.5 g of caprolactone. The reaction mixture was pressurized to 720 kPa (90 psig) of hydrogen and allowed to react at 55° C. for 20 hours to give a 5% conversion to 1,6-hexanediol.

We claim:

1. A process for hydrogenating a monoester to the alcohols corresponding to the acid and alcohol portions of the monoester which comprises reacting hydrogen with the monoester in the liquid phase in the presence of solid catalyst composition at a temperature not exceeding about 150° C., said solid catalyst composition consisting essentially of about 0.1 to about 15 weight percent of at least one group VIII transition metal, about 1 to about 50 weight percent of at least one alkali metal cation, about 2 to about 50 weight percent of an anion radical selected from the group consisting of arene radical anions, ketyls, aliphatic alkoxide anions and mixtures thereof, and the balance of a support comprising high surface area carbon.

2. The process of claim 1 wherein the acid portion of the ester includes an aromatic ring.

3. The process of claim 1 or 14 or 15 wherein the acid portion of the ester is trifluoroacetyl.

4. The process of claim 3 wherein the ester is trifluoroethyl trifluoroacetate.

5. The process of claim 1 wherein the ester is in an inert solvent.

6. The process of claim 5 wherein the inert solvent is a polar ether.

7. The process of claim 6 wherein the inert solvent is tetrahydrofuran.

8. The process of claim 1 wherein the group VIII transition metal is ruthenium, rhodium, platinum or palladium.

9. The process of claim 1 wherein the radical anion is an arene radical anion selected from the group consisting of unsubstituted arene radical anions and arene radical anions substituted with alkyl, ether, dialkylamine or aryl.

10. The process of claim 9 wherein the arene radical anion is an unsubstituted arene radical anion.

11. The process of claim 9 wherein the arene radical anion is the naphthalene radical anion.

12. The process of claim 9 wherein the arene radical anion is the biphenyl radical anion.

13. The process of claim 9 wherein the arene radical anion is selected from the group consisting of the naphthalene, biphenyl, anthracene and phenanthrene radical anions.

14. The process of claim 1 wherein the radical anion is an aliphatic alkoxide radical anion.

15. The process of claim 14 wherein the aliphatic alkoxide anion has at most two carbons and is unsubstituted or substituted by fluorine only.

16. The process of claim 1 wherein the radical anion is a ketyl.

17. The process of claim 16 wherein the ketyl is diaryl ketyl.

18. The process of claim 16 wherein the ketyl is diphenyl ketyl.

19. The process of claim 1 wherein the alkali metal cation is about 2 to about 20 weight percent sodium or potassium cation or about 1 to about 5 weight percent lithium cation.

20. The process of claim 8 wherein the alkali metal cation is potassium cation.

21. A process for hydrogenating a monoester to the alcohols corresponding to the acid and alcohol portions of the monoester which comprises reacting hydrogen with the monoester in the liquid phase at a temperature not exceeding about 150° C. in the presence of a solid catalyst consisting essentially of about 0.1 to about 25 weight percent of at least one group VIII transition metal, about 0.5 to about 60 weight percent of at least one alkali metal and the balance an inert support comprising high surface area carbon.

22. The process of claim 21 wherein the group VIII transition metal is ruthenium, rhodium, platinum, or palladium.

23. The process of claim 22 wherein the group VIII transition metal is ruthenium.

24. The process of claim 22 wherein the group VIII transition metal is rhodium.

25. The process of claim 21 wherein the alkali metal is about 1 to about 5 weight percent lithium or about 2 to about 25 weight percent sodium or potassium.

26. The process of claim 25 wherein the alkali metal is potassium.

27. The process of claim 21 wherein the acid portion of the ester includes an aromatic ring.

28. The process of claim 21 wherein the acid portion of the ester is trifluoroacetyl.

29. The process of claim 28 wherein the ester is trifluoroethyl trifluoroacetate.

30. The process of claim 21 wherein the ester is in an inert solvent.

31. The process of claim 30 wherein the inert solvent is a polar ether.

32. The process of claim 31 wherein the inert solvent is tetrahydrofuran.

* * * * *